United States Patent [19]
Sluka et al.

[11] Patent Number: 5,851,840
[45] Date of Patent: Dec. 22, 1998

[54] BIOTINSILANE COMPOUNDS AND A BINDING MATRIX CONTAINING THESE COMPOUNDS

[75] Inventors: Peter Sluka, Weilheim; Hans-Georg Batz, Tutzing, both of Germany

[73] Assignee: Boehringer Mannheim GmbH, Mannheim-Waldhof, Germany

[21] Appl. No.: 774,579

[22] Filed: Dec. 31, 1996

Related U.S. Application Data

[63] Continuation of Ser. No. 375,035, Jan. 19, 1995, abandoned.

[30] Foreign Application Priority Data

Jan. 19, 1994 [DE] Germany ............... 44 01 450.3
Oct. 6, 1994 [DE] Germany ............... 44 35 728.1

[51] Int. Cl.$^6$ ............... G01N 33/553; C07D 495/04
[52] U.S. Cl. ............... 436/525; 128/899; 424/423; 436/500; 436/527; 436/806; 436/823; 548/304.1; 558/419
[58] Field of Search ............... 436/527, 525, 436/823, 500, 806; 128/899; 424/423; 548/304.1; 558/419

[56] References Cited

U.S. PATENT DOCUMENTS

| | | | |
|---|---|---|---|
| 4,081,245 | 3/1978 | Polito | 23/230.6 |
| 4,128,629 | 12/1978 | Eldred et al. | 424/1 |
| 4,410,633 | 10/1983 | Hertl et al. | 436/500 |
| 4,833,093 | 5/1989 | Malmqvist et al. | 436/527 |
| 5,240,602 | 8/1993 | Hammen | 210/635 |
| 5,405,766 | 4/1995 | Kallury et al. | 435/174 |

FOREIGN PATENT DOCUMENTS

| | | |
|---|---|---|
| 314127 | 5/1989 | European Pat. Off. . |
| 0037081 | 10/1989 | European Pat. Off. . |
| 8302669 | 8/1983 | WIPO . |
| 8807683 | 10/1988 | WIPO . |
| 9116425 | 10/1991 | WIPO . |
| 9208133 | 5/1992 | WIPO . |
| 9210757 | 6/1992 | WIPO . |

OTHER PUBLICATIONS

Analytical Letter, 23(3), 411–424, 1990, Dr. L. Angermaier A Novel Instrumental Set–Up for In–Situ Detection of Protein Adsorption With Grating Coupler Sensors (GCS).

Biophysical Jrl., vol. 60, Sep. 1991, R. Barner et al., Direct Optical Immuno Sensors (Sensivity and Selectivity).

Analytical Bio. 145, 106–112, (1985), Hans Arwin et al., A Reflectance Method For Quantification of Immunological Reactions on Surfaces.

Science, vol. 252, May 1991, Kevin Prime et al., Self–Assembled Organic Monolayers: Model Systems For Studying Adsorption of Proteins at Surfaces.

Colloids and Surfaces B: Biointerfaces I (1993) 107–117, P.W. Wojciechowski et al., Fibrinogen and Albumin Adsorption from Human Blood Plasma and From Buffer onto Chemically Functionalized Silica Substrates.

Fed. Pro vol. 30, No. May 10, 1971, Vincent L. Gott, et al., Antithrombogenic Surfaces, Classification and in Vivao Evaluation on Surfaces.

Vol. XXVI, Trans. Am. Soc. Artif. Intern Organs 1980, H. Bayer et al., Properties of Porous Glass Membranes With Respect to Application In Blood Purification.

Pharmazeutische Technologie, pp. 169–175.

Tetrahedron Letters, 32(14), 1715–18 (1991), Richard T. Pon "A Long Chain Biotin Phosphoramidite Reagent For the Automated Synthesis of 5'–Biotinylated Oligonucleotides".

*Primary Examiner*—Mary E. Ceperley
*Attorney, Agent, or Firm*—Felfe & Lynch

[57] ABSTRACT

The invention concerns a binding matrix containing a carrier material with an oxidic surface and a solid phase reactant covalently bound thereto via anchor groups which is capable of binding to at least one free reaction partner, which is characterized in that the solid phase reactant forms a diluted and essentially laterally homogeneous binding layer on the surface of the carrier material and that the anchor groups are silane groups and are linked to the solid phase reactant via a spacer molecule.

62 Claims, No Drawings

BIOTINSILANE COMPOUNDS AND A BINDING MATRIX CONTAINING THESE COMPOUNDS

This application is a continuation of application Ser. No. 08/375,035, filed Jan. 19, 1995, abandoned.

The present invention concerns a binding matrix containing a carrier material with an oxidic surface and a solid phase reactant which is covalently bound thereto by means of anchor groups and which is capable of binding to at least one free reaction partner wherein this solid phase reactant forms a diluted binding layer on the surface of the carrier material. The present invention in addition concerns new silane compounds, in particular biotinsilane compounds.

Molecular recognition reactions involve the stable and specific binding of two molecules which occurs without the formation of a covalent atomic bond. For practical purposes those reactions are of particular interest which occur at the interface between a solid carrier material and a fluid environment. For this the surface of the solid carrier material is covered with an immobilizing layer which contains a solid phase reactant. The actual recognition reactions then proceed on this immobilizing layer.

An example of such a recognition reaction is a solid phase immunoassay which is carried out by means of an antibody immobilized on the solid phase. This antibody must adhere firmly to the surface of the solid phase in various washing processes and nevertheless have an adequately high immunological activity. Plastic surfaces, preferably made of polystyrene, are usually used as solid phases for immunoassays. Two types of binding are decisive for the usability of the solid phase as a binding matrix for a molecular recognition reaction, namely on the one hand the highest possible binding of specific antibodies which are for example applied adsorptively to polystyrene and, on the other hand, the lowest possible unspecific binding of components of a sample liquid, e.g. blood and serum components such as albumin and in particular fibrinogen.

The unspecific binding of proteins to surfaces is caused by hydrophobic, polar or charge transfer interactions as well as by hydrogen bridge bonds in which the one or other type of binding dominates depending on the type of protein. This unspecific binding of proteins poses a big problem for diagnostic tests, e.g. for solid phase immunoassays and also for medical implants. In the past a very large number of proposals have been published in the literature to solve the problem of unspecific protein binding. However, in all described methods only a partial elimination of the unspecific binding is achieved or a shift from one type of binding to another (cf. e.g. Baeyer et al., Trans. Am. Soc. Artif. Intern. Organs 26 (1980), 309; Gott et al., Federation Proceedings 30 (1977), 5, 1679; Wojciechowski et al., Colloids and Surfaces B: Biointerfaces 1 (1993), 107–117).

Whitesides et al (Science 252 (1991), 1164–1166) showed that an unspecific binding of fibrinogen to metal surfaces can be completely suppressed on gold or silver surfaces by the self assembly of thiols that are functionalized with oligoethylene oxide units.

As already mentioned, the unspecific binding of proteins plays an important role in diagnostics especially in solid phase immunoassays. An immobilizing layer made of streptavidin which can be used for a large number of immunotests by binding to biotin or biotinylated reactants has proven to be particularly advantageous as a solid phase for such applications because it can be used universally. A particularly good adsorption was achieved by using streptavidin bound to polymerized albumin. A surface active agent can be added to suppress unspecific binding to this solid phase (WO88/07683).

However, in new test systems, such as e.g. optical biosensors, plastic surfaces are often unsuitable as solid phases. Carrier materials with an oxidic surface e.g. $SiO_2$ or $TiO_2$ are of particular interest for these applications. Various methods for immobilizing immunologically active substances have also been described for these solid phases. Since oxidic surfaces are normally too hydrophilic for a direct adsorptive coating, the coating is either carried out adsorptively after making the surface hydrophobic (WO91/16425, Anal. Biochem. 145 (1985), 106–112), by light induction (EP-A-0337081) or covalently by means of an appropriate functionalization of the surface (Sensor 91, Kongress Vol. IV).

A binding matrix is disclosed in the PCT application WO 92/10757 which contains a carrier material and a solid phase reactant which is adsorbed thereto via anchor groups and which is capable of binding to at least one free reaction partner wherein the solid phase reactant forms a diluted and essentially laterally homogeneous binding layer on the surface of the carrier material. Metallic surfaces such as gold are described as solid phases and biotinthiols as solid phase reactants. The dilution of the binding layer on the surface can be achieved by co-adsorption of a biotinthiol and of a non-biotinylated thiol. This binding matrix is able, in the case of a suitable mixture of biotin component and diluent, to specifically bind a streptavidin monolayer with a layer thickness of 4 nm on the surface. The unspecific binding of streptavidin is avoided by suitable selection of the diluent.

A disadvantage of the binding matrix described in WO 92/10757 is that an adsorptive coating on hydrophilic surfaces can only be achieved with great difficulty. A continuous bleeding of the protein layer, was observed particularly in the presence of surface-active agents. This also applies to some extent to hydrophobized surfaces.

In addition to the application in solid phase immunoassays, unspecific protein bindings on oxidic surfaces are also relevant in a number of further applications, in particular for example in the case of surfaces of blood filters and glass components in medical instruments (e.g. dialysis instruments) which come into direct contact with blood or blood components, in all types of implants (e.g. hip joints, heart valves) which are composed of titanium or titanium alloys or ceramics as well as in the case of cannulae and surgical instruments. The unspecific attachment of proteins is the primary step towards encapsulation of the implants and limits their residence period in the body to ca. 10 years (Ullmann, "Enzyclopädie der chemischen Technik", Vol. 18, page 169 ff).

Unspecific binding to oxidic surfaces is also relevant in the case of chromatographic materials, carrier materials for peptide or oligonucleotide syntheses and in the case of laboratory glass materials which come into direct contact with blood (centrifuge tubes etc.). The problem of undesired adsorption to hydrophilic surfaces also exists outside of medicine e.g. for car windscreens and crockery.

All previously described methods for reducing or suppressing adsorption to oxidic surfaces have various disadvantages as set forth above. Especially immunological tests on oxidic surfaces exhibit substantial problems of bleeding of adsorptively bound antibodies and in the case of covalent binding of an uncontrolled stoichiometry and in addition problems of unspecific protein adsorption.

The technical problem which forms the basis of the present invention was therefore to modify oxidic surfaces in such a way that the problem of an unspecific adsorption of proteins is eliminated or at least considerably reduced.

One aspect of the present invention concerns the provision of a binding matrix based on a carrier material with an oxidic surface in which the bleeding of solid phase reactants and the unspecific adsorption of proteins is reduced.

It was completely surprisingly found that the unspecific binding of proteins, in particular the unspecific binding of fibrinogen, can be greatly reduced or completely eliminated when oxidic surfaces are functionalized with particular reactive silane compounds. For this purpose the oxidic surface is reacted with compounds which have surface reactive silane terminal groups as anchor groups for reaction with the solid phase and an alkoxy(oligoalkylene oxide) group or a solid phase reactant group wherein the anchor group is linked to the solid phase reactant group or to the alkoxy(oligoalkylene oxide) group via a spacer molecule.

Furthermore, it was found that a binding matrix produced in this manner can be covered reproducibly and controllably with a defined amount of solid phase reactants wherein the solid phase reactants can in turn serve as the basis for a reproducible covering with one or several layers of free reaction partners. An analytical element is obtained in this manner which, like the binding matrix, can serve to detect free analytes.

Moreover the binding matrix or the analytical element does not only have a constant homogeneity over larger surface zones (macrohomogeneity) but also within very small surface zones (microhomogeneity). Therefore it is possible to produce compartmented binding matrices or analytical elements in a simple manner which are excellently suitable for multiple analyte detection.

Thus a first aspect of the present invention concerns a binding matrix containing an anchor material with an oxidic surface and a solid phase reactant which is covalently bound thereto by means of anchor groups and which is capable of binding to at least one free reaction partner, which is characterized in that the solid phase reactant forms a diluted and essentially laterally homogeneous binding layer on the surface of the carrier material and the anchor groups are silane groups that are linked to the solid phase reactant via a spacer molecule.

In a preferred embodiment the diluted monolayer is composed of one type of molecule in which case the surface is not completely covered. The degree of coverage with the solid phase reactant which is a measure of the "dilution" can be expressed as the quotient of the found thickness of the monolayer divided by the theoretical layer thickness for a dense packing.

The degree of coverage of the monolayers with the solid phase reactant is less than 100%, preferably 0.1 to 90% particularly preferably 0.5 to 70%, most preferably 1 to 40%.

Due to the relatively large distance between the individual molecules of the solid phase reactant on the surface of the carrier material, the binding matrix according to the invention contains a more dispersed layer compared to the close packed layer of the state of the art. The diluted monolayer on the surface of the binding matrix according to the invention enables a more rapid binding of the free reaction partner from a fluid phase and, surprisingly, is distinguished by a higher binding capacity.

The carrier material of the binding matrix according to the invention has an oxidic surface. Examples of oxidic surfaces are oxides of metals or semimetals (e.g. B or Si) in the form of pure oxides or mixtures thereof (e.g. glass). Specific examples are $SiO_2$, $TiO_2$, $Al_2O_3$, $Fe_2O_3$, $Ag_2O$, $Cr_2O_3$, $Ta_2O_5$ and mixtures thereof, in which case $SiO_2$, $TiO_2$ and mixtures thereof are particularly preferred.

The covalent binding of the solid phase reactant to the surface of the carrier material is mediated by anchor groups. The anchor groups are surface reactive silane terminal groups i.e. groups in which one or several silicon atoms with substituents are present which can react with an oxidic surface. Examples of such substituents are alkoxy, in particular $C_1$–$C_4$ alkoxy groups and halogen, in particular chlorine atoms. A particularly preferred reactive terminal group is a silane group having the general formula (I):

$$R^1R^2R^3Si— \tag{I}$$

in which $R^1$, $R^2$ and $R^3$ can be the same or different and represent substitutents of the silicon atom provided that at least one of the substituents $R^1$, $R^2$ and $R^3$ can react with an oxidic surface. Specific examples of silane terminal groups of the general formula (I) are monoalkoxydialkylsilane, dialkoxymonoalkylsilane, trialkoxysilane or trihalogensilane groups in which the alkyl and alkoxy residues preferably have 1 to 4 C atoms, particularly preferably 1 or 2 C atoms and most preferably 1 C atom. Preferred specific examples are therefore monomethoxydimethylsilane, dimethoxymonomethylsilane, trimethoxysilane and chlorosilane terminal groups. The silane group (I) is preferably a trifunctional group i.e. all 3 substituents can react with the oxidic surface e.g. trimethoxysilane.

On the other hand the anchor group can also be formed by reaction of the oxidic carrier material surface with a surface reactive silane group of the general formula (II):

in which $R^1$, $R^2$, $R^3$ and $R^4$ correspond to the definition given in formula I provided that at least one of the substituents $R^1$ and $R^2$ or $R^3$ and $R^4$ can covalently bind to an oxidic surface. Specific examples of reactive silane terminal groups of formula (II) are tetramethyldisilanoxy or tetramethoxydisilanoxy groups. The silane group (II) is preferably a tetrafunctional group i.e. all 4 substituents can react with the oxidic surface, e.g. tetramethoxydisilanoxy.

The anchor group is linked to the solid phase reactant via a spacer molecule, preferably via a flexible linear spacer molecule with a chain length of 2 to 50, in particular 4 to 40 atoms. The spacer molecule particularly preferably comprises an alkylene group which is optionally substituted or/and contains heteroatoms. It is expedient to use only those atoms or groups as substituents which cannot covalently bind to the oxidic surface e.g. halogen atoms or double bonded oxygen. Examples of heteroatoms are in particular N, O and S, N and O being preferred.

The anchor group which is covalently bound to the surface of the carrier material is located on one side of the spacer molecule. On its other side, i.e. facing away from the carrier material the spacer molecule contains one or several linking groups via which the solid phase reactant or a component thereof is linked to the spacer molecule. These linking groups can for example be an amino or hydroxyl function which for example is linked to a carboxyl function of the solid phase reactant with formation of an ester or amide group. However, the spacer molecule can also contain a carboxyl function as the linking group which then in turn is linked to a reactive amino or hydroxyl function of the solid phase reactant.

A preferred method of producing a binding matrix according to the invention is to incorporate a hydrophilic linker group between the spacer molecule and the solid phase reactant. This linker is in particular a straight-chained molecule with a chain length of 4 to 15 atoms. In this case a linker group is preferred which contains one or several hydrophilic ethylene oxide units, preferably between 1 and 5. The hydrophilic linker group is particularly preferably comprised of an amine or hydroxyl terminated polyethylene oxide. 1,8-diamino-3,6-dioxaoctane (DADOO) has proven to be a particularly suitable linker.

A further spacer molecule which is defined as above can optionally be incorporated between the hydrophilic linker and the solid phase reactant.

It should be made clear that there are several possibilities for producing a binding matrix according to the invention with a diluted monolayer of the solid phase reactant. Some of these possibilities are set forth in the following, however, this list is not intended to limit the scope of the invention.

A first possibility of producing the diluted binding matrix according to the invention is to select suitable coating conditions. Thus it is possible to achieve a suitable dilution of the binding layer on the surface of the carrier material by variation of parameters such as the concentration of the solid phase reactant that is brought into contact with the oxidic surface, the reaction conditions such as temperature, reaction period or the reactivity of the anchor groups of the solid phase reactant. With regard to these parameters it is established that the density of coverage of the solid phase reactant on the surface of the carrier material increases with an increase in the concentration of the solid phase reactant, the reaction temperature, the reaction period and the reactivity of the anchor groups whereas conversely a reduction in the density of coverage can be achieved by decreasing these parameters. Reaction conditions that are suitable for producing a diluted binding matrix are described in detail in the following.

In a further embodiment of the invention the production of a diluted binding layer of the solid phase reactant can be achieved by simultaneously binding molecules of the solid phase reactant and diluent molecules to the surface of the carrier material.

In this embodiment the binding matrix according to the invention additionally contains spacer molecules which, although provided with an anchor group, do not have a solid phase reactant bound to them. Such compounds are also denoted diluent molecules in the following. If for example biotinylated and non-biotinylated spacer molecules are used in a ratio of 1:10 to 1:2, then one obtains a diluted biotin monolayer which can bind the free reaction partners at a high rate and with a large capacity.

Suitable diluent molecules contain an anchor group and a spacer component as well as if desired a linker molecule wherein the chain length of the spacer molecule of the diluent molecule should preferably differ by not more than 1–5, preferably not more than 1–2 atoms from the chain length of the spacer molecule that is present bound to the solid phase reactant. It has also proven to be expedient to have a minimum chain length of the diluent molecules of 6 atoms (without anchor group and hydrophilic linker groups).

Instead of the solid phase reactant, a functional group such as e.g. a hydroxyl group, a carboxylic acid group, a carboxylic acid ethyl ester or methyl ester group, a carboxylic acid amide group, a carboxylic acid amide group substituted by 1 or 2 methyl or ethyl groups, a sulfonic acid group, a sulfonamide group or an alkoxyoligoalkylene oxide group in particular a $C_1$–$C_4$ alkoxy($C_2$–$C_4$ alkylene oxide) group with 1–10 alkylene oxide units is preferably located at the end of the diluent molecule that is distant from the anchor group. Methoxyoligoalkylene oxide groups are particularly preferred in which an alkylene oxide group can have 2 to 4 C atoms, most preferably 2 C atoms. The number of alkylene oxide groups is preferably 1 to 10. Most preferred are methoxymonoethylene oxide, methoxydiethylene oxide and methoxytriethylene oxide and methoxytetraethylene oxide groups. Thus a preferred diluent molecule preferably contains an anchor group that is reactive with the carrier material on one side of the spacer component and a hydrophilic terminal group on the other side.

In a further embodiment of the invention a spacer with a solid phase reactant and a spacer without a solid phase reactant can be linked by means of a covalent bond. This linkage is preferably achieved by a Si—O—Si bridge.

In such mixed monolayers which are composed of diluent molecules (spacer molecules without solid phase reactant) and of spacer molecules with solid phase reactant, it is expedient that the proportion of spacer molecules with solid phase reactant is 0.1 to 90 mol %, preferably 0.5 to 50 mol-% and particularly preferably 1 to 40 mol-%.

In all previously known binding films the solid phase reactant is composed of one component. This is preferably biotin or molecules similar to biotin such as desthiobiotin, iminobiotin or HABA (4-hydroxyphenyl-azo-benzoic acid) that also react with streptavidin.

Further examples of suitable solid phase reactants are also, however, antigens or haptens capable of binding to an antibody. In this case the solid phase reactant is preferably a hapten with a molecular weight of 100 to 1200. Suitable are for example steroids (such as e.g. digoxin, digoxigenin, cortisol, oestriol, oestradiol, theophylline, diphenylhydantoin, testosterol, bile acids, progesterone and aldosterone), short-chained peptides (such as e.g. argipressin, oxytocin and bradykinin); fluorescein and its derivatives; T3, T4, aflatoxin, atrazine, plant hormones such as e.g. gibberillins; and alkaloids (such as e.g. reserpine and ajmalicin). Further examples of suitable solid phase reactants are also oligo and polynucleotides that can bind to free nucleic acids with a complementary sequence.

Biotin and biotin derivatives, digoxin, digoxigenin, fluorescein and derivatives as well as theophylline are particularly preferably used as the hapten.

On the other hand the solid phase reactant can also be composed of several components. This is in particular to be understood to mean that an inner component of the solid phase reactant is covalently linked to a spacer molecule and is non-covalently bound to the outer component of the solid phase reactant. In this case the outer component of the solid phase reactant is then capable of binding a free reaction partner. The inner component can for example be biotin and the outer component can for example be streptavidin. Such a binding matrix is in turn capable of binding biotinylated reaction partners from a solution since streptavidin has four binding sites for biotin of which at least two are still free.

A binding layer which contains a solid phase reactant composed of two components is a binding matrix according to the invention when the outer component of the solid phase reactant, i.e. that which is capable of binding to a free reaction partner, (i.e. streptavidin in this special case), forms a diluted layer on the surface of the binding matrix. The inner component of the solid phase reactant preferably forms an undiluted layer on the surface of the binding matrix to which the outer component of the solid phase reactant can attach itself to form a diluted layer.

Thus a close packed biotin monolayer with 100% coverage (which itself does not represent a binding matrix according to the invention) binds streptavidin with a lower covering density. This diluted streptavidin layer then in turn represents a binding matrix according to the invention which can bind a free reaction partner, e.g. a biotinylated antibody, to form a close packed film. A diluted biotin monolayer which has for example been produced by using a solid phase reactant with spacer linker, and which itself represents a binding matrix according to the invention for binding free streptavidin, can bind streptavidin to form a close packed film with 100% coverage. However, the close packed streptavidin layer which results in this process does not in turn represent a binding matrix according to the invention (because it is not flexible) and can bind a reaction partner (e.g. a biotinylated antibody) only to form a ca. 10% covered film.

This principle according to the invention of a diluted solid phase reactant capable of binding can also be extended from biotin-streptavidin binding to other binding pairs such as antibody-antigen etc.

The degree of coverage of the solid phase reactant on the surface of the binding matrix can be determined by measuring the thickness of the binding layer. In this case the measured layer thickness decreases with the degree of coverage of the binding layer.

Surprisingly the advantages of the binding matrix according to the invention are seen particularly well in small surface areas, for example in areas $\leq 0.5$ cm$^2$ and in particular $\leq 0.1$ cm$^2$. In this way it is possible to produce a binding matrix which has a plurality of spatially separated zones or compartments on which the binding of free reaction partners to the solid phase reactant can be detected separately from one another using locally resolving detection methods both qualitatively as well as quantitatively.

The present invention therefore also concerns a compartmented binding matrix which is characterized in that a plurality of spatially separated or discrete zones is arranged on a carrier material which each comprise a binding matrix according to the invention.

The spatially separated zones or spots are preferably mounted next to one another in a regular pattern on a common carrier material surface. 10–100 spots per cm$^2$ surface of the carrier material are advantageous and 20–50 spots are particularly advantageous. The diameter of the spots is preferably 0.1–1 mm. The distance between the outer limits of the individual spots is preferably 0.1–1 mm in order to facilitate a separate application of reagents.

The spatially separated surface zones, each comprising a binding matrix, are preferably mounted on a carrier material with a non-oxidic surface. The zones or spots are preferably mounted in a regular pattern. In order to obtain the desired pattern of oxide spots on the carrier material surface, a mask can be placed on the carrier material when the spots are applied in which the desired pattern is left free. The mask can subsequently be treated with vapourized oxidic material or sputtered therewith to form a pattern of oxide spots on the non-oxidic carrier material.

Oxide spots can also be prepared by covering an oxidic surface with non-oxidic material in such a way that the non-oxidic material forms the intermediate areas between individual spots of the oxidic material. Subsequently the oxide spots are coated on the carrier surface with the diluted binding matrix according to the invention. In an embodiment of the present invention the spatially separated oxide spots contain binding matrices each having the same solid phase reactant in which the degree of dilution of the solid phase reactant on the individual spots can be varied if desired. On the other hand, the individual spatially separated oxide spots can also comprise binding matrices with different solid phase reactants.

A further aspect of the present invention is an analytical element which contains a diluted binding matrix wherein the solid phase reactant is covered with one or several additional layers of reaction partners. surprisingly it was namely found that a first free reaction partner can bind very reproducibly and homogeneously to the solid phase reactant of the binding matrix according to the invention. Surprisingly even the amount of the reaction partner can be varied over a wide range by means of the degree of dilution of the solid phase reactant.

After a defined amount of the first free reaction partner has bound to the binding matrix, the resulting analytical element can in turn very readily and reproducibly bind further specific reaction partners in a further layer.

Thus for example a binding matrix according to the invention which contains biotin as the solid phase reactant can be reproducibly coated with streptavidin and this streptavidin layer can in turn be coated very reproducibly with a layer of a biotinylated free reaction partner. The bindable reaction partner on the solid phase reactant is preferably a specific binding partner with bioaffinity which can be used to detect free analytes present in a sample solution. Examples of suitable bindable reaction partners are for example antibodies, antigens, haptens or nucleic acids.

In one embodiment a compartmented binding matrix which contains a plurality of spatially separated spots, each with diluted binding layers of a solid phase reactant, can be used directly for the reproducible application of one or several further layers of the same or different reaction partners.

In another embodiment the diluted binding layers of the individual spots are each covered by a further binding layer. Since this covering according to the invention is reproducible even on a very small area, these binding layers are very well suited for the reproducible covering of an adjustable amount of a third binding layer with reaction partners that can be the same within the analytical element or different from spot to spot.

In both embodiments each spot of the analytical element can be covered separately with a defined amount of reaction partner without unspecific bindings interfering with this covering. Even if the spots have very small dimensions it is possible to achieve a homogeneous covering. By this means it is possible to produce analytical elements with a plurality of spots which have a constant and homogeneous covering of a reaction partner in a very small space. In addition the covering of the various spots with the reaction partner can be simply and reproducibly regulated by means of the degree of dilution of different binding layers so that each spot can be adjusted individually with regard to the analyte to be detected and with regard to the sensitivity which is necessary for this.

A preferred embodiment of the invention is therefore a multiple analytical element based on a compartmented binding matrix which enables a concurrent qualitative or/and quantitative determination of a multitude of analytes in a sample or of one analyte in different samples in a small space and requires only very small amounts of reagent so that there is only very little interference of these determinations by unspecific binding of blood and serum components such as e.g. fibrinogen. Compared to conventional multiparameter analytical elements such as e.g. microtitre plates it is possible in this case to arrange a much higher number of analytical zones on a given area. Thus up to 100 binding matrix spots per cm$^2$ can be arranged without difficulty.

The compartmented analytical element according to the invention can be based on a binding matrix with the same or different solid phase reactants. A preferred embodiment is a compartmented analytical element based on one binding matrix which contains the same solid phase reactant on every spot. Each spot can in turn be used for the spatially limited and reproducible, homogeneous binding of optionally different free reaction partners.

The present invention in addition concerns an analytical element for the determination of different analytes in a sample comprising a compartmented binding matrix in which the individual spatially separated binding matrix zones are each covered with different reaction partners capable of binding to the solid phase reactant. Yet a further object of the present invention is an analytical element for the determination of the same analyte in different samples comprising a compartmented binding matrix in which the individual spatially separated binding matrix zones are each covered with the same reaction partner capable of binding to the solid phase reactant.

The multianalyte analytical elements according to the invention preferably comprise a laminar carrier material the surface of which is covered with a regular pattern on spatially separated zones which each contain a binding matrix that is covered with one or several layers of additional reaction partners.

The present invention in addition concerns a process for the production of a binding matrix according to the invention. Due to the different nature of the binding matrices according to the invention the details of the production processes are also different. Several preferred variants of these production processes are described in the examples of operation. In general the process according to the invention comprises the incubation of the carrier material with a reaction solution in which molecules are present which form the binding layer of the binding matrix according to the invention. Opposite sides of these molecules contain the anchor group and the solid phase reactant (although in some embodiments of the present invention not all molecules of the binding layer have to be linked to a solid phase reactant). The solid phase reactant is preferably linked via a spacer molecule to the anchor group. The binding of the anchor groups to the carrier material from the solution to form the binding matrix according to the invention is a spontaneous process.

The coating of oxidic surfaces with silanes is carried out by contacting a solution of the silane compound or of a mixture of silane compounds with a previously cleaned oxidic surface. The cleaning of the oxidic surface is preferably carried out by boiling in a strong inorganic acid e.g. $HNO_3$, $H_2SO_4$, HCl and particularly preferably aqua regia ($H_2SO_4$/HCl). Subsequently the oxidic surface is washed to remove the acid and dried. Then the surface which has been cleaned in this manner is brought into contact with the solution of silane compound. Anhydrous organic solvents such as methanol, chloroform or mixtures thereof are suitable as the solvent. In addition it is preferred that the binding layer is applied under a protecting gas e.g. $N_2$.

When the silanization of the oxidic surface is incomplete in order to produce a diluted binding layer of the solid phase reactant without using a silane diluent, the concentration of the solid phase reactant-silane compound is preferably $10-4$ to $10-2\%$ by weight in a suitable solvent, particularly preferably $5\times10^{-3}\%$ by weight to $5\times10^{-2}\%$ by weight. The reaction period is preferably 10 to 60 minutes, particularly preferably 20 to 40 minutes and the temperature of the reaction is preferably 10° to 50° C., particularly preferably room temperature.

If it is intended to coat the oxidic surface with a combination of biotinsilane and silane diluent, the concentration of the silane compounds in the solvent is preferably 0.1 to 5% by weight, particularly preferably 0.5 to 2% by weight in which case the individual compounds can be used in the respective desired proportions. The reaction period is preferably 1 to 8 hours, particularly preferably 3 to 5 hours. The temperature is preferably 10° to 50° C., particularly preferably room temperature.

After the reaction has been carried out, the surfaces are subsequently rinsed, preferably with the solvent used to apply the silane and conditioned in an oven if desired under a vacuum for a period of 20 minutes to 8 hours at an elevated temperature e.g. 60° to 140° C.

If desired, a further substance can be attached in a second step by incubation with a second reaction solution particularly when the solid phase reactant is composed of several components that are non-covalently linked to one another. The reaction conditions are not critical for the application of the second and optional further layers so that it can be carried out without protecting gas and with water as the solvent.

The binding layer produced by the process according to the invention is microscopically homogeneous which can be tested by suitable methods such as waveguide measurements or white-light interferometry.

The present invention in addition concerns a process for the production of a compartmented binding matrix in which spatially separated zones on a carrier material which have an oxidic surface are incubated with the same or different reaction solutions that contain molecules that are composed of surface-active silane terminal groups and are linked thereby via spacer molecules to the same or different solid phase reactants. The spatially separated zones with an oxidic surface are preferably attached to a carrier material with a non-oxidic surface by for example applying a mask and treating with vapourized or sputtered oxidic material.

If the zones or spots of the compartmented binding matrix are intended to be the same, the carrier element can simply be immersed in a reaction solution which contains the molecules necessary for producing the desired binding matrix. If, however, the binding matrices of the individual zones are intended to be different, then different reaction solutions are applied to the individual oxide spots each of which contains other solid phase reactants. Instead of this or in addition thereto it is also possible to produce different degrees of dilution of the binding matrices on the various spots by for example a different proportion of diluent molecules being present in the individual reaction solutions that are applied to different spots. This spatially separate application of the reaction solutions can be carried out by conventional methods such as pipetting, stamping or printing techniques such as e.g. ink-jet.

Yet a further subject matter of the present invention is a process for the production of an analytical element wherein a binding matrix according to the invention is incubated with at least one reaction solution which contains molecules of further reaction partners capable of binding to the binding matrix.

Compartmented analytical elements can be manufactured in different ways. In the simplest case a solution of the same or different reaction partners is applied, for example with a pipette, to different binding matrix spots each of which is covered with a diluted binding layer. These reaction partners must be able to bind to the solid phase reactant at the surface of the compartmented binding matrix. Therefore conjugates are preferably used as the reaction partners that contain a group capable of binding to the solid phase reactant. An example of such conjugates is antibodies that are coupled to biotin. On different oxide spots which are covered with a diluted biotin-silane binding matrix and with a steptavidin binding layer bound thereto, it is possible to apply the same or different biotinylated antibodies to the individual spots which then bind to the individual streptavidin layers. In this manner an analytical element is obtained which has different zones in the minimum of space which, if desired, are able to bind many different free analytes.

If the same biotinylated antibody is applied to each spot then it is possible to determine several samples concurrently with the analytical element which contain an analyte that is reactive with the antibody bound to the solid phase.

Further possibilities for applying different reaction partners on the respective spots are printing or stamping techniques, in particular ink-jet or application by means of a micromultipin plate similar to the application of different reagents on microtitre plates.

In addition the present invention concerns a method for the determination of an analyte in a sample solution by means of a specific binding reaction between at least two reactants having bioaffinity one of which is present coupled to a solid phase and the other partner or partners are free, wherein a solid phase reactant is used which is a component of a binding matrix according to the invention.

In such a method the detection of binding of the free reaction partner to the solid phase reactant can be facilitated by the fact that the free binding partner carries a marker group. It is particularly common to label with an enzyme or with a fluorescent or luminescent component. The indirect optical observation of the binding which this facilitates enables an exact quantitative detection.

In principle the binding can be detected by optical or electrochemical means and even by means of heat tonality or formation of mass. In the case of electrochemical techniques, potentiometric or amperometric methods come into particular consideration such as those that are described for example in "Biosensors", Turner, Karube, Wilson (eds.), Oxford Press, 1987 or Bergveld, Biosensors & Bioelectronics 6, 55–72 (1991). Determinations by means of electrical conductivity or change in capacitance are also possible as electrochemical techniques.

However, the detection of binding is preferably carried out by optical, in particular optical reflection techniques, in which the increase in the layer thickness of an extremely thin layer containing the reactant immobilized on the carrier caused by binding of the free binding partner can be observed. A review of these techniques is given in Sadowski: "Review of optical methods in immunosensing", SPIE, vol. 954 Optical testing and Metrology II (1988), 413–419.

A particularly preferred optical reflection method is the detection of the binding by waveguide measurements and white-light interferometry.

The waveguide measurement method is described in Anal. Let. 23 (3), 411–424 (1990) and is based on the fact that laser light is coupled into a waveguiding layer over a grating on the sensor. The coupling conditions (angle) depend on the conditions at the interfaces of the waveguiding layer. Thus the thickness of the binding layer on the surface can be deduced from changes in the coupling conditions.

A further suitable method for determining the layer thickness of the binding matrix according to the invention is white-light interferometry. Such measurement systems are marketed by the Carl Zeiss Company, Oberkochen, Germany. The measurement system for white-light interferometry is composed of a diode array spectrometer, an illumination device, preferably a Y light conductor with 2 light conducting bundles which are collected at one end and statistically mixed and also of a reflection optical system.

When a compartmented binding matrix or a compartmented analytical element is used, the concurrent determination of different, i.e. of at least two analytes in a sample solution, or the concurrent determination of one analyte in different sample solutions is possible. Therefore a subject matter of the present invention is a method for the concurrent determination of different analytes in a sample solution which is characterized in that the sample solution is brought into contact with a compartmented binding matrix or with a compartmented analytical element and the presence or/and the amount of the different analytes in the sample solution is determined by locally resolving measurement at the individual, spatially separated binding matrix zones.

In order to detect the binding of the analytes on individual adjacent spots qualitatively and also quantitatively, locally resolving methods of detection are used. A preferred method is confocal fluorescence microscopy. In this method a fluorescent dye used for labelling is excited to fluorescence on each spot individually with the aid of a laser that emits a suitable wavelength. The emitted light is registered by means of sensitive detectors such as e.g. integrated CCD cameras and it is quantified with suitable computer software for image analysis. Other methods of fluorescence microscopy are also well-suited for the analysis. In this case several spots are observed simultaneously in one section of the image. The individual spots are then analysed for example successively with the aid of suitable image analysis software.

In addition the analysis can also be carried out with the aid of the already described optical reflection techniques. Other locally resolving detection methods such as electrochemical methods, conductivity measurement or the measurement of radioactive labels are possible.

In order to analyse a sample for different analytes, the sample can either be applied over a large area of the compartmented binding matrix or the compartmented analytical element or separately on individual spots. If necessary further labelled binding partners for the analytes to be determined are also added. In this case the analytical element is preferably washed free of non-bound marker molecules before measurement of the labelled analytes bound to the solid phase.

The compartmented binding matrix or the compartmented analytical element can also be used for the concurrent determination of analytes in different samples. A subject matter of the invention is therefore also a method for the concurrent determination of one analyte in different sample solutions which is characterized in that in each case a sample solution is brought into contact with individual zones of a compartmented binding matrix or of an analytical element and the presence or/and the amount of the analyte in each sample solution is determined by locally resolving measurement at the individual spatially separated binding matrix zones. The determination is preferably carried out by means of specific binding reactions of the analyte to the solid-phase-bound analyte binding partners and by separate measurement of the individual binding matrix zones. The various sample solutions can in this case be applied by conventional application techniques such as pipetting, printing or stamping techniques or multipin plates. In this manner it is possible to concurrently measure many samples on very small areas.

The binding matrix according to the invention and the analytical element according to the invention can thus be used extremely well for multiple analyte detection i.e. for the simultaneous detection of a multitude of analytes or for the simultaneous detection of one analyte in a multitude of samples in particular for immunoassays for example for allergy diagnostics or DNA diagnostics e.g. to screen a sample for nucleic acids with particular sequences.

A further subject matter of the invention is a silane compound having one of the general formulae (III) or (IV)

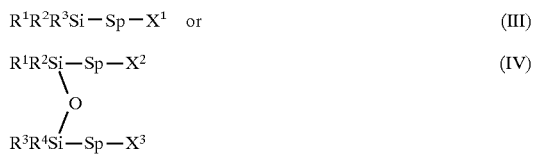

in which $R^1$, $R^2$, $R^3$, $R^4$ can be the same or different and denote substituents on the Si atom provided that at least one of the substituents $R^1$, $R^2$ and $R^3$ in formula (III) or at least one of the substituents $R^1$ and $R^2$ or $R^3$ and $R^4$ in formula (IV) can covalently bind to an oxidic surface, Sp is a flexible linear spacer molecule with a chain length of 2 to 50 atoms and $X^1$, $X^2$, $X^3$ are solid phase reactants that are covalently bound to the spacer molecule or/and $C_1$–$C_4$ alkoxy (oligo $C_2$–$C_4$ alkylene oxide) groups.

The residues $R^1$, $R^2$, $R^3$ and $R^4$ in the silane groups of compounds (III) and (IV) are preferably $C_1$–$C_4$ alkyl groups, $C_1$–$C_4$ alkoxy groups, hydroxy groups, amino groups or halogen atoms. $R^1$, $R^2$, $R^3$ and $R^4$ are particularly preferably $C_1$–$C_2$ alkoxy groups and most preferably methoxy groups.

If $X^1$, $X^2$, $X^3$ denote solid phase reactants they are preferably biotin or a biotin derivative. Sp preferably comprises an alkylene group which, if desired, is substituted or/and contain heteroatoms.

Surprisingly the unspecific binding of proteins e.g. fibrinogen to oxidic surfaces can be suppressed by covalent binding of the silanes according to the invention to the surface and in particular those with methoxyoligoethylene glycol terminal groups.

A further subject matter of the present invention is therefore a process for reducing unspecific protein binding to oxidic surfaces which is characterized in that the oxidic surface is treated with one or several silanes according to the invention in which $X^1$, $X^2$, $X^3$ in the formulae (III) or (IV) are $C_1$–$C_4$ alkoxy(oligo $C_2$–$C_4$-alkylene oxide) groups. The alkoxy groups are preferably $C_1$–$C_2$ alkoxy groups, particularly preferably methoxy groups. The $C_2$–$C_4$ alkylene oxide groups are preferably ethylene oxide and/or propylene oxide groups, particularly preferably ethylene oxide groups. The alkoxyoligoalkylene oxide groups preferably have 1 to 10 and particularly preferably 1 to 6 alkylene oxide units.

In addition it is preferred that the oxidic surfaces are treated with silanes of the general formula (III) i.e. with silane compounds which have a $R^1,R^2,R^3$ Si terminal group. Preferably all the substituents $R^1,R^2,R^3$ and $R^4$ in formulae (III) and (IV) are such reactive atoms or groups that can react with the oxidic surface, in particular $C_1$–$C_4$ alkoxy groups and most preferably methoxy groups.

Finally the invention also concerns an object with an oxidic surface which is characterized in that the oxidic surface is at least partially covered by a binding layer which is formed by reaction of one or several silanes according to the invention having the general formulae (III) and (IV) with the surface wherein $X^1$, $X^2$ and $X^3$ in formulae (III) or (IV) are $C_1$–$C_4$ alkoxy(oligo $C_2$–$C_4$ alkylene oxide) groups.

The binding layer is preferably a saturated layer i.e. a layer that is close packed with the silanes. The object according to the invention is preferably a medical article which is intended for direct contact with blood or other body fluids.

An oxidic surface modified according to the invention can be used in particular for medical implants e.g. artificial hip joints, heart valves and, due to suppression of unspecific attachment of proteins, the period in which the implants can be retained in the body is considerably longer compared to known products. Moreover such surfaces can also be used in medical instruments which come into direct contact with blood or blood components e.g. dialysis instruments, cannulae, surgical instruments etc., chromatographic materials, support materials for chemical peptide or oligonucleotide synthesis etc. and other objects for which it is intended to prevent an unspecific binding of proteins.

It is intended to elucidate the invention further by the following examples.

EXAMPLE 1

Synthesis of biotinsilane 1

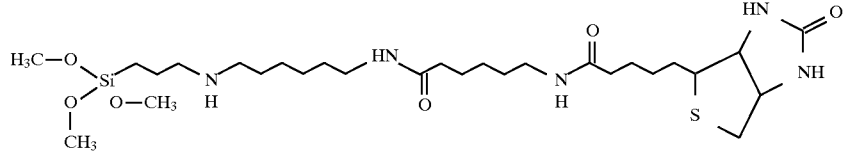

2.0 g biotinoyl-ε-aminocaproic acid-N-hydroxysuccinimide ester (biotin-X-OSu) was suspended in 40 ml methanol. 1.0 g 6-(aminohexylaminopropyl)-trimethoxysilane was added dropwise and the solution was stirred for 1½ hours at room temperature. The methanol was subsequently removed by distillation. The product was subsequently purified by column chromatography. 1.3 g of a white solid was obtained.

EXAMPLE 2

Synthesis of biotinsilane 2

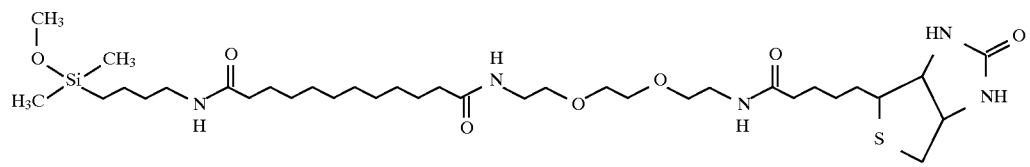

2.1 Synthesis of biotin-DADOO-dodecanoic acid-OSu ester 560 mg biotin-DADOO was dissolved in 30 ml DMF and it was added dropwise together with 150 ml triethylamine to a solution of 6.36 g dedecanoic acid bis-OSu ester. The solution was stirred for 3 hours at room temperature, subsequently the solvent was withdrawn to a large extent and the residue was chromatographed over Sephadex.

2.2 Synthesis of biotinsilane 2

280 mg of the isolated biotin-DADOO-dodecanoic acid OSu ester was dissolved in 5 ml methanol. 80 mg aminobutyldimethylmethoxysilane was added dropwise to the solution and stirred for 1 hour. 30 ml diethyl ether was subsequently added to the solution and the precipitated solid was filtered by suction. Purification was carried out by means of chromatography on $NH_2$-silica gel. The yield was 50 mg.

EXAMPLE 3
Synthesis of biotinsilane 3

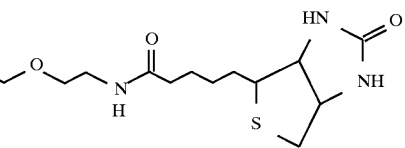

680 mg of the biotin-DADOO-dodecanoic acid OSu ester was dissolved in 7 ml methanol. 215 mg aminopropyltrimethoxysilane was added dropwise to the solution and stirred for 1 hour. The solution was subsequently purified over a $NH_2$-silica gel column. The product fractions were concentrated, admixed with 50 ml diethyl ether and the precipitated solid was suction filtered. The yield was 420 mg.

EXAMPLE 4
Synthesis of the silane diluent 4

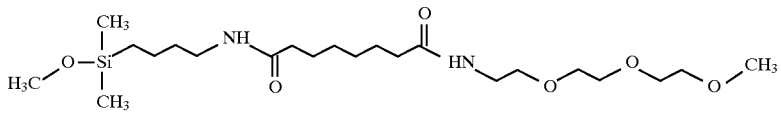

4.1 Synthesis of triethylene glycol monomethyl ethertosylate 69.6 g tosyl chloride was slowly added at −5° C. to a solution of 53.2 ml triethylene glycol monoethyl ether in 400 ml pyridine. It was stirred for 3 hours at 0° C. and for 1 hour at room temperature. The preparation was admixed with 400 ml water and subsequently extracted with ethyl acetate. 90 g of the tosylate (85% yield) was isolated from the ethyl acetate phase.

4.2 Synthesis of triethylene glycol monomethyl etherphthalimide 9.55 g of the tosylate was dissolved in 20 ml DMF and added dropwise to a solution of 6.11 g phthalimide, potassium salt in 80 ml DMF. The mixture was stirred for 4 hours at 120° C., subsequently diluted with water and extracted with ethyl acetate. 4.7 g of the product in the form of an oil was isolated from the ethyl acetate phase (53%).

4.3 Synthesis of 1-amino-triethylene glycol monomethyl ether 1.53 g of the product isolated under 4.2 was dissolved in 25 ml methanol. 0.32 ml 80% hydrazine hydrate solution was added dropwise and boiled under reflux for 3 hours at 50° C. and subsequently for 15 min. The mixture was subsequently acidified with HCl and filtered after cooling. The filtrate was neutralized and subsequently extracted with chloroform. 740 mg of the product 1-amino-triethylene glycol monomethyl ether was isolated from the chloroform phase in the form of an oil (87% yield).

4.4 Synthesis of suberic acid-1-OSu-ester-12-amidotriethylene glycol monomethyl ester 15.8 g suberic acid bis-OSu ester was dissolved together with 0.6 ml triethylamine in 20 ml DMF. 700 mg of the product isolated under 4.3 was added to this solution in 10 ml DMF. The preparation was stirred for 4 hours at room temperature and subsequently the DMF was withdrawn. The residue was admixed with 20 ml water and subsequently filtered. The filtrate was freed of solvent and subsequently purified over a silica gel column. The product was obtained as an oil in a yield of 750 mg (42%).

4.5 Synthesis of 4

270 mg of the product from 4.4 was dissolved in a mixture of 5 ml diethyl ether and 1 ml methanol. 0.09 ml triethylamine was added and subsequently 115 mg amino-butyl-dimethylmonomethoxysilane was added dropwise. It was stirred for 1 hour at room temperature and the product was subsequently purified by means of chromatography. 190 mg (63%) of the silane diluent 4 was obtained.

Example 5

5.1 Synthesis of the silane diluent 5

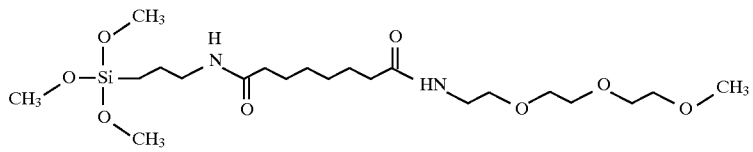

270 mg of the product from 4.4 was dissolved in a mixture of 5 ml diethyl ether and 1 ml methanol. 0.09 ml triethylamine was added and subsequently 127 mg aminobutyltrimethoxysilane was added dropwise. Subsequently it was stirred for 1 hour at room temperature and the product was then purified by means of chromatography. 190 mg (61%) of the silane diluent 5 was obtained.

5.2 Synthesis of the silane diluent 6

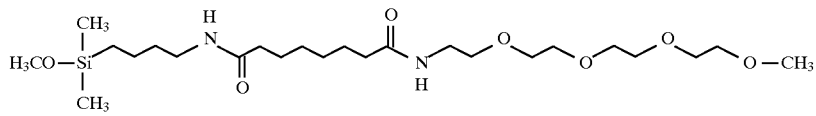

The synthesis of this silane was carried out completely anagously to the synthesis previously described for 4. Tetraethylene glycol monomethyl ether was used as the starting substance instead of triethylene glycol monomethyl ether.

5.3 Synthesis of the silane diluent 7

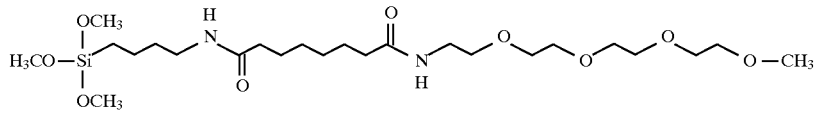

The synthesis of this silane was carried out completely analogously to the already described synthesis of 5. Tetraethylene glycol monomethyl ether was used as the starting substance instead of triethylene glycol monomethyl ether.

EXAMPLE 6

In addition the following silane compounds were prepared:

6.1 Biotinsilane compound 8

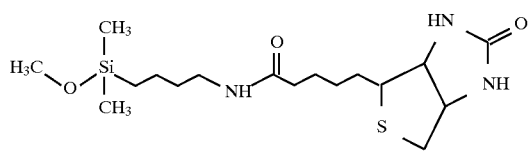

6.2 Biotinsilane compound 9

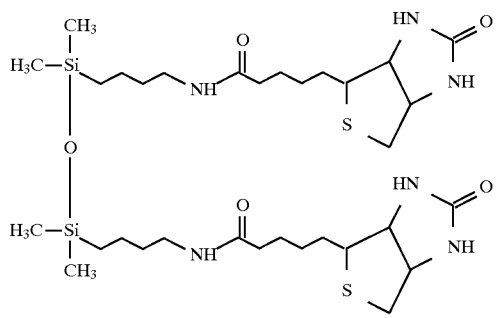

6.3 Biotinsilane compound 10

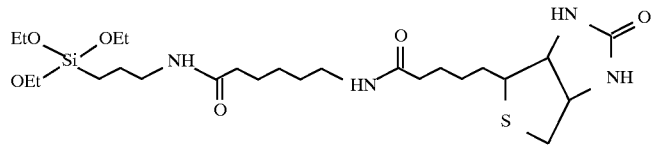

6.4 Biotinsilane compound 11

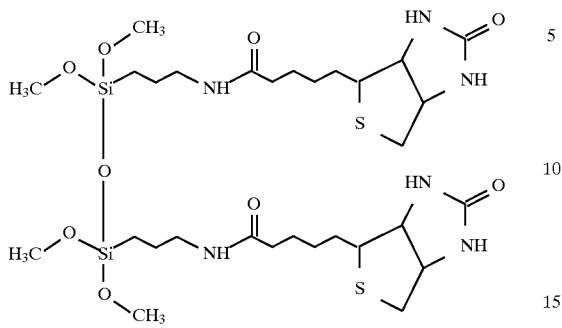

6.5 Biotinsilane compound 12

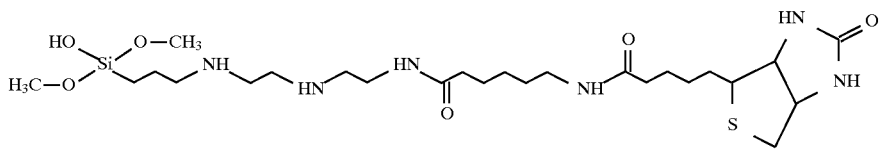

6.6 Biotinsilane compound 13

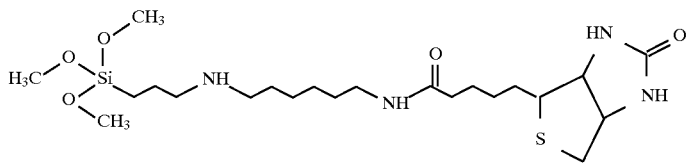

1.7 g biotin-X-OSu was suspended in 20 ml methanol and 1.28 g 6-(aminohexylaminopropyl-trimethoxysilane was added dropwise thereto. The solution was stirred for 1.5 hours and subsequently it was chromatographed over an amino-silica gel column. 2.1 g of a white solid was obtained.

6.7 Biotinsilane compound 14

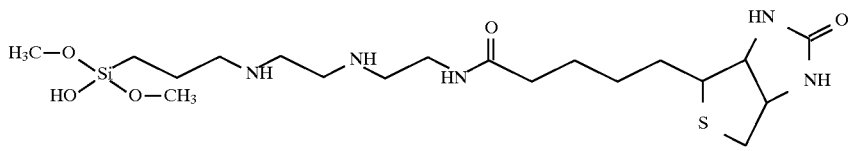

6.8 Biotinsilane compound 15

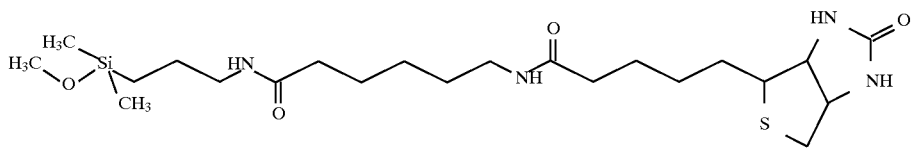

850 mg biotin-X-OSu was suspended in 10 ml methanol and 280 mg 4-aminobutyldimethylmethoxysilane was added dropwise to this suspension. The solution was stirred for 4 hours at room temperature and subsequently purified by means of an amino-silica gel column. 700 mg of a white solid was obtained.

6.9 Biotinsilane compound 16

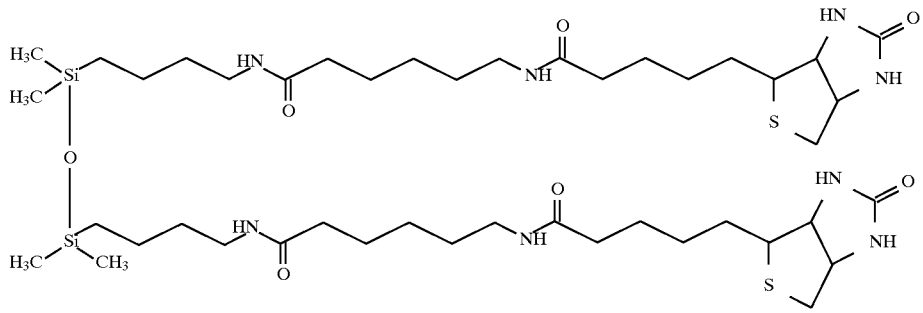

20

6.10 Biotinsilane compound 17

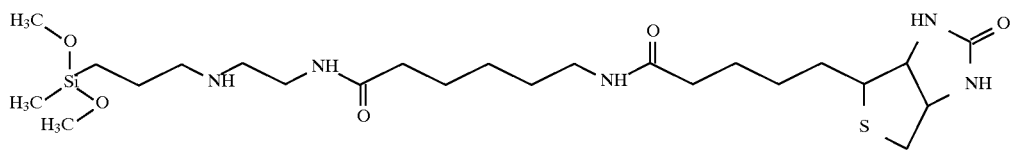

30

800 mg biotin-X-OSu was suspended in 20 ml methanol. 300 mg (2-aminoethylamino)propylmethyldimethoxysilane was added dropwise thereto and it was stirred for 2.5 hours. The preparation was subsequently purified over an amino-silica gel column. 650 mg product was obtained.

6.11 Biotinsilane compound 18

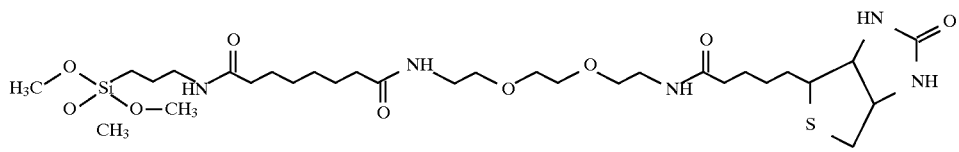

6.12 Biotinsilane compound 19

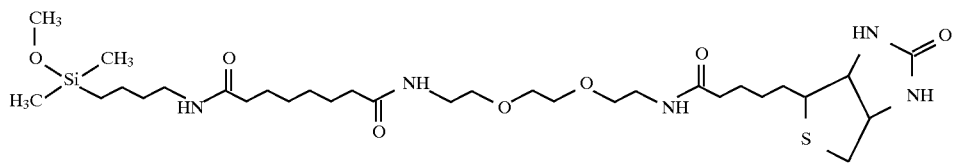

6.13 Biotinsilane compound 20

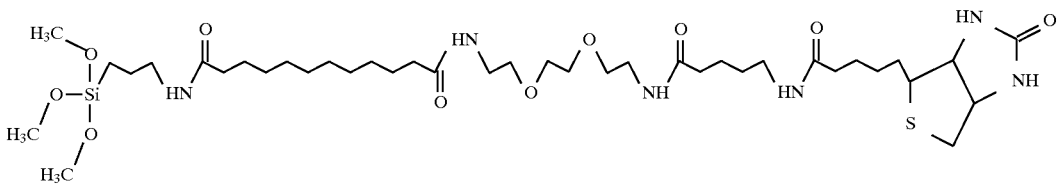
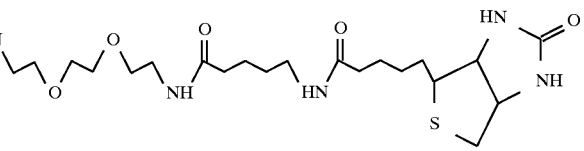

6.14 Biotinsilane compound 21

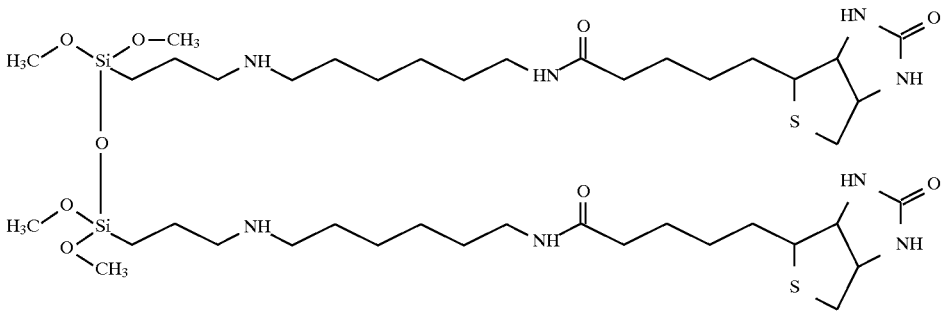

6.15 Silane diluent 22

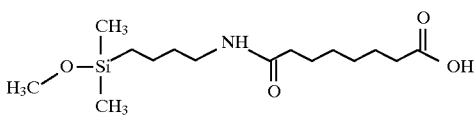

6.16 Silane diluent 23

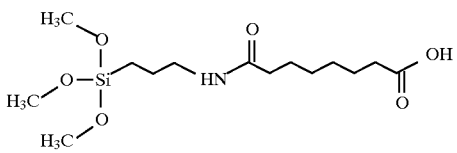

EXAMPLE 7

Methods for analysing the surfaces 7.1 Waveguide measurements

The measurements were carried out on sensors and instruments from the ASI (Artificial Sensing Instruments, Zurich) Company. In the measurement laser light is coupled into a waveguiding layer over a grating on the sensor. The coupling conditions (angle) depend on the conditions at the interfaces of the waveguiding layer. Thus the layer thicknesses of the growing layers can be deduced from the change in the coupling conditions. The measurements were carried out in flow cuvettes. The waveguiding layer is a mixed oxide composed of $SiO_2/TiO_2$.

7.2 White-light interferometry (WIF)

The measurements were carried out on a Zeiss measuring arrangement with a Zeiss CLX-111 white light source and a Zeiss MCS-310 diode array spectrometer as the detector unit. Schott colour filter glasses WG 345 were used as sensors which were coated in a Leybold coating apparatus Univex 450 with ca. 800 nm $SiO_2$. The measurements were carried out in flow cuvettes. The layer thicknesses can be determined from the interferograms obtained.

EXAMPLE 8

Application of biotinsilanes on oxidic surfaces 8.1 Preparing the surfaces

The oxidic surfaces to be coated were boiled for several minutes in aqua regia, subsequently washed three times with redistilled water and dried for one hour at 80° C. in a vacuum.

8.2 Incomplete silanization of surfaces to produce a diluted biotin layer without using a silane diluent Silane 1 is dissolved at a concentration of $10^{-3}\%$ by weight in dry methanol. The test piece to be coated which had been prepared according to 8.1 is immersed in this solution and kept in the solution for 30 minutes at room temperature. The surfaces are subsequently rinsed three times with dry methanol and conditioned for 30 minutes at 80° C. in a vacuum.

8.3 Process for coating oxidic surfaces with biotinsilanes, hydrophilic diluents or mixed layers of both Silanes or mixtures thereof are dissolved in dry methanol at a total concentration of 1% by weight according to their molar proportions in the mixtures. The test piece to be coated which had been prepared according to 8.1 is coated with this solution in a closed vessel under a methanol-saturated inert gas atmosphere. The reaction time is 4 hours at room temperature. The surface is subsequently rinsed with methanol and the sample is conditioned for 4 hours at 120° C. in a drying cupboard.

EXAMPLE 9

Results of the analyses (white light interferometry)

In the case of white-light interferometry measurements protein solutions were pumped through a teflon cuvette by means of a Pharmacia peristaltic pump. Each of the cycles was 10 minutes with 5 minute intervals for intermediate rinsing (i.e. 10 min buffer, 10 min protein solution 1, 5 min buffer, 10 min protein solution 2, etc.).

9.1 Solutions used

Buffer: PBS buffer (50 mM potassium phosphate, 150 mM NaCl, pH 7.2)

streptavidin solution: c=0.5 mg/ml in PBS biotin-<HCG>-Fab fragment (Bi-Fab): c=0.1 mg/ml in PBS human chorionic gonadotrophin (HCG): c=5 μg/ml bovine fibrinogen: c=3 mg/ml

9.2 Binding of fibrinogen

It is measured using WIF, 10 minutes PBS buffer, 10 minutes fibrinogen solution, 10 minutes PBS buffer.

9.2.1 Uniformly functionalized surfaces (not a mixed layer)

All silanes were applied according to 8.3 except fluorosilanes and trichloro-octadecylsilane. Chloroform was used as the solvent for fluorosilane and trichlorooctadecylsilane.

| Surface | Layer thickness (nm) |
| --- | --- |
| untreated $SiO_2$ | 4.0 |
| $SiO_2$ + silane diluent 5 | 0.0 |
| $SiO_2$ + silane diluent 4 | 2.0 |
| $SiO_2$ + silane diluent 6 | 2.0 |
| $SiO_2$ + silane diluent 7 | 0.0 |
| $SiO_2$ + biotinsilane 1 | 4.1 |
| $SiO_2$ + biotinsilane 2 | 3.8 |
| $SiO_2$ + 3-aminopropyltrimethoxysilane (Aldrich) | 3.5 |
| $SiO_2$ + N-[trimethoxylsilyl) -propyl]ethylene-diaminotriacetic acid-$Na_3$ salt (ABCR) | |
| pH 7.2 | 1.3 |
| pH 9.0 | 1.2 |
| pH 3.0 | 7.5 |
| $SiO_2$ + 1H, 1H, 2H, 2H-perfluorodecyltrichloro silane (ABCR) | 2.6 |
| $SiO_2$ + 1H, 1H, 2H, 2H-perfluorodecyldimethyl chlorosilane (ABCR) | 2.0 |
| $SiO_2$ + trichloro-octadecylsilane (Merck) | 3.5 |

9.2.2 Surfaces with a mixed layer

| $X_B$ | Biotinsilane 1/ diluent 5 layer thickness (nm) | Biotinsilane 2/ diluent 4 layer thickness (nm) | Biotinsilane #1/ diluent 7 layer thickness (nm) |
| --- | --- | --- | --- |
| 0.0 | 0.0 | 2.0 | 0.0 |
| 0.05 | 0.6 | 1.2 | 0.0 |
| 0.1 | 0.6 | 2.0 | 0.0 |
| 0.2 | 0.0 | 2.0 | 0.0 |
| 0.5 | 0.7 | 2.3 | 2.3 |
| 1.0 | 4.1 | 3.8 | 4.1 |

$X_B$ mole fraction of the biotin component

9.3 Specific Binding of Streptavidin

| $X_B$ | Biotinsilane 1/ diluent 5 layer thickness (nm) | Biotinsilane 2/ diluent 4 layer thickness (nm) | Biotinsilane #1/ diluent 7 layer thickness (nm) |
| --- | --- | --- | --- |
| 0.0 | 0.0 | 1.1 | 0.0 |
| 0.05 | 1.8 | 0.9 | 1.0 |
| 0.1 | 3.8 | 1.2 | 0.5 |
| 0.2 | 6.0 | 1.7 | 0.5 |
| 0.5 | 4.9 | 2.9 | 1.0 |
| 1.0 | 4.5 | 3.4 | 2.6 |

9.4 Unspecific Binding of Streptavidin

Streptavidin saturated with biotin was passed over the sensor surface.

| Sensor | Increase in layer thickness (nm) |
| --- | --- |
| Diluent 5/Biotinsilane 1 ($X_B$ = 0.2) | 0.0 |
| Diluent 5/Biotinsilane 1 ($X_B$ = 0.5) | 0.0 |
| Diluent 4/Biotinsilane 2 ($X_B$ = 0.5) | 1.5 |

9.5 Procedure for HCG Immunotests

Sensors coated with streptavidin were coated with a biotinylated <HCG> Fab fragment. Subsequently the HCG solution was passed over the sensor.

| Sensor | Layer thicknesses (nm) | | |
| --- | --- | --- | --- |
| | Streptav. | Bi-Fab | HCG |
| Diluent 5/Biotinsilane 1 $X_B$ = 0.1 | 3.8 | 1.7 | 0.4 |
| Diluent 5/Biotinsilane 1 $X_B$ = 0.2 | 6.0 | 2.3 | 0.6 |

EXAMPLE 10

Results of the analysis using waveguide technology (ASI)

The ASI sensors were coated with the biotinsilane compounds 1, 13, 15 and 17. The coating was carried out without the use of a diluent according to the method described in item 8.2. The binding capability of streptavidin to these sensors was analysed as well as the proportion of unspecifically bound streptavidin.

The layer thickness of the sensors was smaller after the coating with biotinsilanes than before the coating (between 0.01 and 0.81 nm). The angles of coupling (TM+) and (TE+) were likewise decreased by the coating.

The proportion of unspecific binding of streptavidin to the silanized ASI sensor surface in relation to the total streptavidin binding was very variable depending on the biotinsilane compound:

| 17 | 24% |
| --- | --- |
| 15 | 73% |
| 1 | 9% |
| 13 | 20% |
| MeOH | 91% |

17, 1 and 13 bind streptavidin well (→no bleeding).

The proportion of unspecific binding of Bi-MAB<TSH> (in the presence of biotin) to a streptavidin surface saturated with biotin was also variable for all biotinsilanes:

| 17 | 20% |
| --- | --- |
| 15 | <100% |
| 1 | 42% |
| 13 | 31% |
| MeOH | 24% |

17 was the best of the examined biotinsilane compounds. Sensors treated with 17 gave the highest signal amplitude for analytes (TSH).

EXAMPLE 11

Use of a microcompartmented binding matrix in an immunoassay

11.1 Production of $SiO_2$ spots by vapourization

36x36 round spots of $SiO_2$ (a total of 1296 spots) were vapourized at regular intervals onto "Lexan" polycarbonate foils (manufacturer: General Electric, thickness: 0.75 mm) with dimensions of 8×8 cm by means of a metal mask (d=0.5 mm, aluminium material) in a Leybold high-vacuum coating apparatus (Univex 450) by means of electron beam vapourization. The layer thickness of the vapour-coated oxide is 150 mm. The diameter of the spots is 1 mm, the distance from one spot to another is also 1 mm in all directions.

11.2 Application of biotinsilanes onto the spots

A mixture of silane 1 and silane 5 in a molar ratio of 1/9 was dissolved in methanol to a total concentration of 1% by weight. 1% water was added to this solution and the substrate with the spots was immersed in this solution. The reaction time was 4 hours. After this time the plate was washed with methanol and dried for 4 hours at 120° C.

11.3 Application of streptavidin

The plates coated with the spots in this way were overlayered for one hour with a streptavidin solution in 50 mmol/l K-phosphate buffer, pH 7.2 (c=0.5 mg/ml). Afterwards the plate was washed with a solution of 50 mmol/l K-phosphate buffer pH 7.2, 2% sucrose, 0.9% NaCl and 0.3% bovine serum albumin and subsequently dried for 20 hours at 25° C. and 40% humidity in a climatic chamber.

11.4 Procedure for a TSH test

A TSH test was carried out according to the following scheme on the spots coated with streptavidin:

1. incubate with the biotinylated monoclonal anti-TSH antibody 1.20 Bi (OSu) 1:8 for 45 minutes. The concentration of the antibody was 10 µg/ml, buffer: 20 mmol/l K-phosphate pH 7.4.
2. wash with buffer
3. incubate for minutes with the "Enzymun" standard, Boehringer Mannheim Company or with a plasma sample.
4. wash with buffer
5. incubate for minutes with fluorescent latex-antibody (A8) conjugate (batch DF499), 0.02% solids content in buffer
6. wash with buffer
7. measure in a confocal fluorescence microscope (Biorad company).

11.5 Results

2 Standards (0 µU and 2.3 µU as well as a plasma sample with 3.2 µU TSH) were measured. The following relative intensities were obtained in this way:

| Sample | rel. intensities |
|---|---|
| 0 µU TSH | 26.4 |
| 2.3 µU TSH | 112.7 |
| Plasma (3.2 µU TSH) | 186.7 |

We claim:

1. Binding matrix comprising an oxidic surface, wherein the oxidic surface is at least partially covered by a diluted and essentially laterally homogeneous binding layer, said binding layer formed by covalent reaction of a silane compound with the oxidic surface, said silane compound selected from the group consisting of:

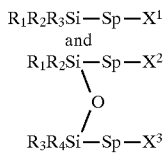

wherein $R_1$, $R_2$, $R_3$ and $R_4$ are the same or different and are substituents on the Si atom, provided that at least one of the substituents is covalently bound to the oxidic surface, and wherein said substituents are selected from the group consisting of $C_1$–$C_4$ alkyl, $C_1$–$C_4$ alkoxy, hydroxy, amino and halogen; Sp is a flexible, linear spacer molecule with a chain length of 2 to 50 atoms, and $X^1 X^2$ and $X^3$ are each solid phase reactants capable of binding to an analyte in a sample, wherein said binding matrix further comprises diluent molecules which are covalently bound to the oxidic surface but are incapable of binding to the analyte.

2. The binding matrix of claim 1, wherein the coverage of the solid phase reactant on the oxidic surface is 0.1 to 90% of maximum coverage.

3. The binding matrix of claim 2, wherein the coverage of the solid phase reactant on the oxidic surface is 0.5 to 70% of maximum coverage.

4. The binding matrix of claim 3, wherein the coverage of the solid phase reactant on the oxidic surface is 1 to 40% of maximum coverage.

5. The binding matrix of claim 1, wherein the flexible, linear spacer molecule comprises a moiety selected from the group consisting of a substituted alkylene group and an alkylene group which contains heteroatoms.

6. Binding matrix as claimed in claim 1, wherein a hydrophilic linker group is located between the spacer molecule and the solid phase reactant.

7. Binding matrix as claimed in claim 6, wherein the hydrophilic linker group contains one or more oxyethylene groups.

8. Binding matrix as claimed in claim 7, wherein the hydrophilic linker group is formed by an aminoterminated or hydroxyl-terminated polyethylene oxide.

9. Binding matrix as claimed in claim 8, wherein the hydrophilic linker group is formed from 1,8 diamino-3,6-dioxaoctane.

10. The binding matrix of claim 1, wherein said diluent molecules comprise an alkoxyoligoalkylene oxide terminal group.

11. Binding matrix as claimed in claim 1, wherein the solid phase reactant is an antigen or hapten capable of binding to an antibody.

12. The binding matrix of claim 1, wherein the solid phase reactant is biotin or a biotin derivative.

13. The binding matrix of claim 1, wherein the solid phase reactant is composed of an inner component covalently linked to the spacer molecule and an outer component noncovalently linked to the inner component, the outer component being capable of binding to an analyte in a sample.

14. The binding matrix of claim 13, wherein the inner component of the solid phase reactant forms an undiluted layer on the oxidic surface and the outer component is coupled to the inner component by affinity binding.

15. Binding matrix as claimed in claim 14, wherein the inner component is biotin and the outer component is streptavidin.

16. Compartmented binding matrix, comprising a plurality of spatially separated zones, each zone comprising the binding matrix of claim 1.

17. Compartmented binding matrix of claim 16 wherein the plurality of spatially separated zones, are arranged on a non-oxidic surface.

18. Compartmented binding matrix as claimed in claim 16, wherein the spatially separated zones comprise binding matrices each with the same solid phase reactant.

19. Compartmented binding matrix as claimed in claim 16, wherein the spatially separated zones comprise binding matrices with different solid phase reactants.

20. Analytical element comprising the binding matrix of claim 1, wherein the solid phase reactant is covered with one or several additional layers consisting of reaction partners, the reaction partners in the additional layer being able to bind to analytes in a sample.

21. The analytical element of claim 20, wherein the reaction partners are selected from the group consisting of antigens, haptens, antibodies and nucleic acids.

22. Analytical element for the determination of different analytes in a sample, comprising the compartmented binding matrix of claim 16, wherein the solid phase reactants of the individual spatially separated binding matrix zones are each covered with different reaction partners able to bind to an analyte in a sample.

23. Analytical element for the determination of the same analyte in different samples, comprising the compartmented binding matrix of claim 16, wherein the individual solid phase reactants of the spatially separated binding matrix zones are each covered with the same reaction partners, said reaction partners being able to bind to the same analyte in a sample.

24. Method for the determination of an analyte in a sample solution comprising providing a binding matrix comprising an oxidic surface wherein the oxidic surface is partially covered by a diluted and essentially laterally homogeneous binding layer, said binding layer formed by covalent reaction of a silane compound with the oxidic surface, said silane compound selected from the group consisting of:

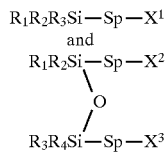

wherein $R_1$, $R_2$, $R_3$ and $R_4$ are the same or different and are substituents on the Si atom, provided that at least one of the substituents is covalently bound to the oxidic surface, wherein said substituents are selected from the group consisting of $C_1$–$C_4$ alkyl, $C_1$–$C_4$ alkoxy, hydroxy, amino and halogen; Sp is a flexible, linear spacer molecule with a chain length of 2 to 50 atoms, and $X^1$, $X^2$ and $X^3$ are each solid phase reactants capable of binding to an analyte in a sample, wherein said binding matrix further comprises diluent molecules which are covalently bound to the oxidic surface but incapable of binding to the analyte in a sample, and contacting said binding matrix with a solution containing said analyte, said analyte having a bioaffinity for the solid phase reactant of the binding matrix, under conditions favoring binding of said analyte to said binding matrix; and detecting the bound analyte.

25. The method of claim 24, wherein the bound analyte is detected by waveguide measurements or by white-light interferometry.

26. Method for the concurrent determination of different analytes in a sample solution, comprising contacting the sample solution with at least one member selected from the group consisting of:

(a) a compartmented binding matrix comprising a plurality of spatially separated zones, each zone comprising a binding matrix having an oxidic surface, wherein the oxidic surface is at least partially covered by a diluted and essentially laterally homogenous binding layer, said binding layer formed by covalent reaction of a silane compound with the oxidic surface, said silane compound selected from the group consisting of:

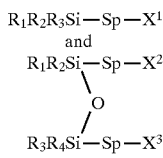

wherein $R_1$, $R_2$, $R_3$ and $R_4$ are the same or different and are substituents on the Si atom, provided that at least on of the substituents is covalently bound to the oxidic surface and said substituents are selected from the group consisting of $C_1$–$C_4$ alkyl, $C_1$–$C_4$ alkoxy, hydroxy, amino and halogen; Sp is a flexible, linear spacer molecule with a chain length of 2 to 50 atoms, and $X^1$, $X^2$ and $X^3$ are each solid phase reactants capable of binding to an analyte in a sample, wherein said binding matrix further comprises diluent molecules which are covalently bound to the oxidic surface but are incapable of binding to any of the analytes, and wherein the spatially separated zones comprise binding matrices with different solid phase reactants, and (b) an analytical element comprising a compartmented binding matrix of (a), wherein the solid phase reactant is covered with one or more layers of reaction partners, said compartmented binding matrix comprising a plurality of spatially separated zones, each of which comprises a binding matrix as in (a), and wherein the individual spatially separated zones are each covered with different reaction partners; and detecting the presence of analyte in said sample solution by locally resolving measurement of individually spatially separated binding matrix zones.

27. Method for the concurrent determination of an analyte in different sample solutions, wherein in each determination a sample solution is contacted with individual zones of at least one member selected from the group consisting of:

(a) a compartmented binding matrix comprising a plurality of spatially separated zones, each zone comprising a binding matrix comprising an oxidic surface, wherein the oxidic surface is at least partially covered by a diluted and essentially laterally homogenous binding layer, said binding layer formed by covalent reaction of a silane compound with the oxidic surface, said silane compound selected from the group consisting of:

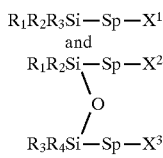

wherein $R_1$, $R_2$, $R_3$ and $R_4$ are the same or different and are substituents on the Si atom, provided that at least one of the substituents is covalently bound to the oxidic surface and said substituents are selected from the group consisting of $C_1$–$C_4$ alkyl, $C_1$–$C_4$ alkoxy, hydroxy, amino and halogen; Sp is a flexible, linear spacer molecule with a chain length of 2 to 50 atoms, and $X^1$, $X^2$ and $X^3$ are each solid phase reactants capable of binding to an analyte in a sample, wherein said binding matrix further comprises diluent molecules which are covalently bound to the oxidic surface but which are incapable of binding to an analyte, and wherein the spatially separated zones comprise binding matrices each with the same solid phase reactant, and (b) an analytical element comprising a compartmented binding matrix of (a), wherein the solid phase reactant is covered with one or more layers of reaction partners, and wherein the spatially separated zones are each covered with the same reaction partners, and detecting the presence of the analyte in each sample solution by locally resolving measurement of individually separated binding matrix zones.

28. Method as claimed in claim 26, wherein the locally resolving measurement is carried out by means of confocal fluorescence microscopy.

29. The binding matrix of claim 1, wherein at least one of said solid phase reactants binds to nucleic acids.

30. A silane compound selected from the group consisting of:

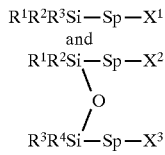

wherein $R^1$, $R^2$, $R^3$, and $R^4$ can be the same or different and are substituents on the Si atom, provided that at least one of the substituents $R^1$, $R^2$, $R^3$ and $R^4$, can covalently bind to an oxidic surface, wherein said substituents are selected from the group consisting of $C_1-C_4$ alkyl, $C_1-C_4$ alkoxy, hydroxy, amino, and halogen, Sp is a flexible, linear spacer molecule with a chain length of 2 to 50 atoms which is covalently bound to the Si atom by an Si—C bond, and $X^1$, $X^2$, $X^3$ are selected from the group consisting of biotin, a biotin analogue, a biotin derivative, a hapten, an oligonucleotide, a polynucleotide, and a $C_1-C_1$ alkoxy(oligo-$C_2-C_4$ alkylene-oxide) group and are covalently bound to the spacer molecule.

31. The silane compound of claim 30, wherein $X^1$, $X^2$, $X^3$ are each biotin or a biotin derivative.

32. The silane compound of claim 30, wherein Sp comprises a moiety selected from the group consisting of an alkylene group attached to a substituent halogen or double bonded oxygen and an alkylene group which contains at least one heteroatom selected from the group consisting of N, O, and S.

33. Process for making an article having an oxidic surface which has decreased unspecific protein binding to oxidic surfaces comprising bringing the oxidic surface into contact with a solution containing diluent molecules comprising at least one silane compound selected from the group consisting of:

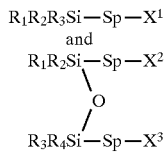

wherein $R^1$, $R^2$, $R^3$ and $R^4$ are the same or different and are substituents on the Si atom, provided that at least one of the substituents $R^1$, $R^2$, $R^3$ and $R^4$ can covalently bind to an oxidic surface, and said substituents are selected from the group consisting of $C_1-C_4$ alkyl, $C_1-C_4$ alkoxy, hydroxy, amino and halogen; Sp is a flexible, linear spacer molecule with a chain length of 2 to 50 atoms which is covalently bound to the Si atom by an Si—C bond, and $X^1$, $X^2$ and $X^3$ are each covalently bound to the spacer molecule, under conditions which lead to a covalent reaction of at least one of said silane compounds with the oxidic surface, and wherein $X^1$, $X^2$, and $X^3$ are $C_1-C_4$ alkoxy(oligo-$C_2-C_4$-alkylene-oxide) groups.

34. Process of claim 33 wherein the oxide surface is treated with silanes of the general formula $R^1 R^2 R^3$ Si-Sp-$X^1$.

35. Process as claimed in claim 33, wherein $X^1$, $X^2$ and $X^3$ are $C_1-C_2$ alkoxy(oligo-ethylene oxide) groups with 1 to 8 ethylene oxide units.

36. Article comprising an oxidic surface, wherein the oxidic surface is covered by a binding layer which is formed by the covalent reaction of diluent molecules comprising at least one silane compound selected from the group consisting of:

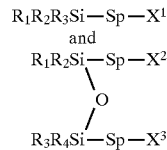

wherein $R^1$, $R^2$, $R^3$ and $R^4$ are the same or different and are substituents on the Si atom, provided that at least one of the substituents $R^1$, $R^2$, $R^3$ and $R^4$ covalently binds to the oxidic surface, wherein said substituents are selected from the group consisting of $C_1-C_4$ alkyl, $C_1-C_4$ alkoxy, hydroxy, amino and halogen; Sp is a flexible, linear spacer molecule with a chain length of 2 to 50 atoms which is covalently bonded to the Si atom by an Si—C bond and $X^1$, $X^2$ and $X^3$ are covalently bound to the spacer molecule, wherein $X^1$, $X^2$ and $X^3$ are $C_1-C_4$ alkoxy(oligo-$C_2-C_4$ alkylene oxide) groups.

37. The article of claim 36 wherein the oxidic surface is covered by a binding layer in which the silane compounds are closely packed.

38. The analytical element of claim 20 wherein at least one of said solid phase reactant binds to nucleic acids.

39. The article of claim 36 wherein the binding layer at least partially covers the oxidic surface.

40. A process for the production of a binding matrix comprising an oxidic surface wherein the oxidic surface is at least partially covered by an essentially laterally homogeneous binding layer said process comprising contacting the oxidic surface with a solution comprising a silane compound selected from the group consisting of:

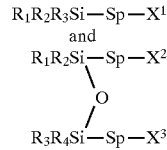

wherein $R_1$, $R_2$, $R_3$ and $R_4$ are the same or different and are substituents on the Si atom, provided that at least one of the substituents is able to covalently bind to the oxidic surfaces, wherein said substituents are selected from the group consisting of $C_1-C_4$ alkyl, $C_1-C_4$ alkoxy, hydroxy, amino and halogen; Sp is a flexible, linear spacer molecule with a chain length of 2 to 50 atoms, and $X^1$, $X^2$ and $X^3$ are each solid phase reactants capable of binding to an analyte in a sample; and diluent molecules capable of covalently binding to the oxidic surface but incapable of binding to an analyte in a sample, wherein said silane compound is present at a concentration of from $10^{-4}$ to $10^{-2}\%$ by weight, under conditions favoring covalent attachment of said silane compound and said diluent molecules to the oxidic surface.

41. A process for the production of a compartmented binding matrix comprising a plurality of spatially separated zones, each zone comprising a binding matrix comprising an oxidic surface, wherein the oxidic surface is at least partially covered by an essentially laterally homogeneous binding layer, said process comprising contacting each oxidic surface of the binding matrices with a solution comprising a silane compound selected from the group consisting of:

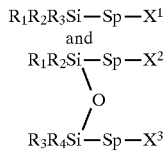

wherein $R_1$, $R_2$, $R_3$ and $R_4$ are the same or different and are substituents on the Si atom, provided that at least one of the substituents is able to covalently bind to the oxidic surfaces; wherein said substituents are selected from the group consisting of $C_1$–$C_4$ alkyl, $C_1$–$C_4$ alkoxy, hydroxy, amino and halogen; Sp is a flexible, linear spacer molecule with a chain length of 2 to 50 atoms, and $X^1$, $X^2$ and $X^3$ are each solid phase reactants capable of binding to an analyte in a sample; and diluent molecules capable of covalently binding to the oxidic surface but incapable of covalently binding to an analyte in the sample, wherein the concentration of the silane compound is $10^{-4}$ to $10^{-2}\%$ by weight, under conditions favoring covalent attachment of said silane compound and said diluent molecules to the oxidic surface.

42. The process of claim 41 wherein the oxidic surfaces are mounted onto a non-oxidic surface.

43. The process of claim 41 comprising said oxidic surfaces with said silane compound by immersion in said solution.

44. The process of claim 41 comprises contacting said oxidic surfaces with different silane compounds by contacting a plurality of said solutions, each of which contains a different silane compound, with said oxidic surfaces.

45. A process for the production of a binding matrix comprising an oxidic surface, wherein the oxidic surface is at least partially covered by a diluted and essentially laterally homogeneous binding layer, said process comprising contacting the oxidic surface with a solution comprising a silane compound selected from the group consisting of:

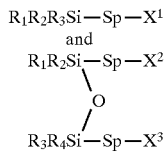

wherein $R_1$, $R_2$, $R_3$ and $R_4$ are the same or different and are substituents on the Si atom, provided that at least one of the substituents is able to covalently bind to the oxidic surface wherein said substituents are selected from the group consisting of $C_1$–$C_4$ alkyl, $C_1$–$C_4$ alkoxy, hydroxy, amino and halogen; Sp is a flexible, linear spacer molecule with a chain length of 2 to 50 atoms, and $X^1$, $X^2$ and $X^3$ are each solid phase reactants capable of binding to an analyte in a sample, said solution also comprising diluent molecules that are capable of binding to the oxidic surface but are incapable of binding to an analyte in the sample, wherein said silane compounds and said diluent molecules are present in said solution in a ratio of 1:10 to 1:2, under conditions favoring covalent attachment of said silane compounds and said diluent molecules to said oxidic surface.

46. A process for the production of a compartmented binding matrix comprising a plurality of spatially separated zones, each zone comprising a binding matrix comprising an oxidic surface, wherein the oxidic surface is at least partially covered by a diluted and essentially laterally homogeneous binding layer, said process comprising contacting the oxidic surface with a solution comprising a silane compound selected from the group consisting of:

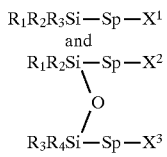

wherein $R_1$, $R_2$, $R_3$ and $R_4$ are the same or different and are substituents on the Si atom, provided that at least one of the substituents is able to covalently bind to the oxidic surface; wherein said substituents are selected from the group consisting of $C_1$–$C_4$ alkyl, $C_1$–$C_4$ alkoxy, hydroxy, amino and halogen; Sp is a flexible, linear spacer molecule with a chain length of 2 to 50 atoms, and $X^1$, $X^2$ and $X^3$ are each solid phase reactants capable of binding to an analyte in a sample, said solution also comprising diluent molecules that are capable of covalently binding to the oxidic surface but are incapable of binding to an analyte in the sample, wherein said silane compounds and said diluent molecules are present in said solution in a ratio of 1:10 to 1:2, under conditions favoring covalent attachment of said silane compounds and said diluent molecules to said oxidic surfaces.

47. The process of claim 46 wherein the oxidic surfaces are mounted onto a non-oxidic surface.

48. The process of claim 46 comprising said oxidic surfaces are with said silane compound and a diluent molecule, by immersion of all the oxide surfaces in said solution.

49. The process of claim 46 comprising contacting said oxidic surfaces with different silane compounds by contacting a plurality of said solutions each of which contains a different silane compound, to each of the said oxidic surfaces.

50. The process of claim 40 further comprising incubating said oxidic surface with a second solution which contains a reaction partner, said reaction partner being capable of binding to the solid phase reactant and to an analyte in a sample.

51. The process of claim 41 further comprising incubating said oxidic surface with a second solution comprising a reaction partner, said reaction partner capable of binding to the solid phase reactant and to an analyte in a sample.

52. The process of claim 42 further comprising incubating the oxidic surface with a second solution comprising a reaction partner, said reaction partner being capable of binding to the solid phase reactant and to an analyte in a sample.

53. The process of claim 43 further comprising incubating the oxidic surface with a second solution comprising a reaction partner, said reaction partner being capable of binding to the solid phase reactant and to an analyte in a sample.

54. The process of claim 44 further comprising incubating the oxidic surface with a second solution comprising a reaction partner, said reaction partner being capable of binding to the solid phase reactant and to an analyte in a sample.

55. The process of claim 45 further comprising incubating the oxidic surface with a second solution comprising a reaction partner, said reaction partner being capable of binding to the solid phase reactant and to an analyte in a sample.

56. The process of claim 46 further comprising incubating the oxidic surface with a second solution comprising a reaction partner, said reaction partner being capable of binding to the solid phase reactant and to an analyte in a sample.

57. The process of claim 47 further comprising incubating the oxidic surface with a second solution comprising a reaction partner, said reaction partner being capable of binding to the solid phase reactant and to an analyte in a sample.

58. The process of claim 48 further comprising incubating the oxidic surface with a second solution comprising a reaction partner, said reaction partner being capable of binding to the solid phase reactant and to an analyte in a sample.

59. The process of claim 49 further comprising incubating the oxidic surface with a second solution comprising a reaction partner, said reaction partner being capable of binding to the solid phase reactant and to an analyte in a sample.

60. The method of claim 24 wherein the solid phase reactant of the binding matrix is covered with additional layers consisting of reaction partners, the reaction partners capable of binding to an analyte in a sample.

61. Implant useful in treating a subject in need thereof, comprising the article of claim 36.

62. Component of a medical instrument comprising the article of claim 36, wherein said component comes into direct contact with body fluids.

* * * * *